US009414894B1

(12) United States Patent
Mansueto

(10) Patent No.: US 9,414,894 B1

(45) Date of Patent: Aug. 16, 2016

(54) COLOR SAFEGUARDED DENTAL-IMPLANT SURGICAL-KIT WITH DRILLING DEPTH LIMITER

(76) Inventor: Robert F. Mansueto, Coronado, CA (US)

( * ) Notice: Subject to any disclaimer, the term of this patent is extended or adjusted under 35 U.S.C. 154(b) by 0 days.

(21) Appl. No.: 12/315,947

(22) Filed: Dec. 9, 2008

(51) Int. Cl.
*A61C 3/04* (2006.01)

(52) U.S. Cl.
CPC .................................... *A61C 3/04* (2013.01)

(58) Field of Classification Search
CPC ............................ A61C 3/04; A61C 2202/00
USPC .......... 433/165–166, 77, 79; 422/300; 606/80
See application file for complete search history.

(56) References Cited

U.S. PATENT DOCUMENTS

| | | | | |
|---|---|---|---|---|
| 5,147,164 | A | 9/1992 | Fraver | 408/202 |
| 5,525,314 | A * | 6/1996 | Hurson | 422/300 |
| 5,741,267 | A | 4/1998 | Jorneus | 606/102 |
| 6,406,295 | B1 | 6/2002 | Mahler | 433/173 |
| 6,764,306 | B1 | 7/2004 | DiMarino | 433/77 |
| 6,863,529 | B2 | 3/2005 | Strong | 433/165 |
| 7,048,477 | B2 | 5/2006 | Abrams | 408/1 R |
| 7,278,852 | B2 * | 10/2007 | Fischer | 433/224 |
| 2002/0172923 | A1 * | 11/2002 | Strong et al. | 433/165 |
| 2006/0188840 | A1 | 8/2006 | Verban, Jr. | 433/75 |

* cited by examiner

*Primary Examiner* — Nicholas Lucchesi

(74) *Attorney, Agent, or Firm* — David B. Waller

(57) ABSTRACT

An apparatus is an implant-dentist more readily identifiable visual segregation amongst their oral-surgery arbor-tools used conjunction with a conventional hand-held power/rotary-tool. The arbor-tools generally has at least a tri-echeloned set, wherein are included progressions of drill-bit lengths and companion thread-taps appearing in three different diameters. Additionally, the drill-bit shanks are optionally provided with a radial-flange serving as an automatic depth-stop device and these radial-flanges may include a distinctive annular-marker device serving to readily indicate the length of the selected drill-bit, thereby obviating usual procedure of stopping to confirm via the obscure conventional alpha-numeric indicia.

4 Claims, 3 Drawing Sheets

COLOR SAFEGUARDED DENTAL-IMPLANT SURGICAL-KIT WITH DRILLING DEPTH LIMITER

FIELD OF THE INVENTION

The present disclosure relates to dental-implant arbor-tool organization, enabling faster and more accurate visual selection; and more specifically, it relates to discrete color-segregation of the arbor-tools and dental-implants according to the different diameters, which procedurally operate in conjunction with the dentists existing conventional hand-held power-driver. Additionally, this disclosure relates to an allied drilling-depth limiting device which also safeguards the oral-preparation procedure while providing demarcation means by which to readily distinguish progressions of drill-bit lengths from amongst a given diametrical family of arbor-tools.

BACKGROUND OF THE INVENTION

Heretofore, the implant-dentist has been confronted with an overwhelming array of oral-surgery arbor-tools, which fit into the rotary-chuck of their hand-held pneumatic/power-driver. These arbor-tools generally constitute a three-echeloned set, wherein are included progressions of drill-hit lengths and companion thread-taps appearing in different diameters; all of which presents an array of pieces, potentially confusing especially to a new implant-dentist. Each of these tiny arbor-tools has a chuck-shank member bearing necessarily diminutive ID-indicia inscription thereon, which thus poses a potential of leading the implant-dentist into inadvertently making a serious procedural mistake. For example, if the implant-dentist were to misread the ID-indicia, and thereby select a larger drill-bit diameter, it would ruin their ability to install the proper dental-implant size. Moreover, it has been found that the conventional delivery-tray confusion also makes the implant-dentist prone to making drilling 'depth' errors, which can be equally problematical to satisfactory preparation of the dental-implant pilot-hole. Accordingly, there is a critical need for an apparatus and system or method by which to prevent such potentially disastrous human-errors known to frequently happen, owing to the presently provided upon the implant-dentists arbor-tools and associated dental-implants.

SUMMARY OF THE INVENTION

In view of the foregoing discussion about the earlier invention art, it is important to make it pellucid to others interested in the art, that the basic object of this invention is to provide color-coded coordinated components within a dental-implant surgical-kit which function to safeguard against inadvertent procedural errors. Moreover, while thus safeguarding against making mistakes, my invention hereof also greatly improves vital time-&-motion procedures, as shall become apparent.

Presently, owing the numerous demands upon an implant-dentist during their intense oral-cavity osteotomy-site preparation operation, the implant-dentist can unknowingly become diverted from a thoughtfully planned course of procedure, while occasionally necessarily re-selecting from amongst a wide array of arbor-tool implement progressions.

For example, the arbor-tools presented upon the implant-dentist's conventional surgical-kit delivery-tray generally comprise a conglomeration of drill-bits, different lengths (e.g.: 8 mm, 10 mm, 12 mm, and 14 mm) generally provided in three or more different diameters (e.g.: 3.4 mm, 4.1 mm and 5.1 mm), plus companion thread-taps and attachment sockets for each diameter. Owing the subtle differences in length and diameter, to the laymen, these arbor-tools would all look pretty much the same; nevertheless, the subtle dimensional differences between these dental arbor-tools become vitally important in relationship to the critical fitting of and ultimately successful osseointegration of a tiny dental-implant.

It is imperative the work-stressed implant-dentist be provided tools which are designed to ease procedures, enabling them to become more focused upon a patient's osteotomy-site preparation. To better appreciate the potential problems an implant-dentist experiences while routinely selecting the desired arbor-tool from a conventional delivery-tray presenting a vast plurality of implements, one must further understand that inscribed upon the upper-shank portion of the implant-dentist's arbor-tools are necessarily extremely diminutive ID-indicia (i.e.: ID='identification'/indicia=alpha-numeric characters) bearing the particular length and diameter of a given drill-bit. This minute dimensional ID-indicia inscription is often faint to read, requiring that the implant-dentist pause, carefully examine their next desired drill-bit selection (as compared to their previously used drill-bit size), then believing they have read the obscure inscription correctly, install the drill-bit into the drill-chuck of their hand-held high-rpm dental power-driver. Without the present invention improvement, the implant-dentist can inadvertently misread or otherwise become momentarily mentally-distracted, thus it is all too easy to execute a serious error, which even though the implant-dentist may be highly skilled, can possibly even become a dreadful medical-malpractice issue.

Accordingly, the inventor hereof has resolved that the implant-dentist's conventional management of their precision arbor-tools is far too confusing, as it involves utilization of a rather bewildering array of drill-bit lengths and diameters which can thereby inadvertently lead the heavily burdened implant-dentist into making serious mistakes, compromising the quality outcome of their critical patient-care task.

Studies of the implant-dentist's arbor-tool selection procedures resulted in an improved apparatus and systematic methodology in the form of the I-Dent™ Surgical-kit, conducted over the last few months via a multi-clinic field-testing program; the success of which is becoming most gratifying, resulting in numerous national field reports expressing strong praise of appreciation as to its effectiveness, from amongst both new and long established implant-dentists alike. The improved surgical-kit delivery-tray provides a unique systematic arrangement of implant-dentist arbor-tools into discrete diametrically uniform groups, hereinafter referred to as 'unidiameter-groups'. For example, all common drill-bits and thread-tap members having in common a 3.4 mm-diameter (including their typical 8 mm, 10 mm, 12 mm, 14 mm length progressions) thus comprise a discrete unidiameter-group having a permanent factory-applied distinct external color of 'green' for example; moreover, the next unidiameter-group of such arbor-tool implements having in common a 4.1 mm-diameter would (merely by way of example herein only) exhibit a distinctively different external color of 'amber', while all 5.1 mm-diameter arbor-tools might also for example exhibit an externally distinguishing color 'violet'. However, for purposes of this disclosure, it must also be regarded that one of the distinguishing colors of the arbor-tools can remain the natural 'grayish' shade of the base titanium material from which it is generally constituted, as clearly, the objective herein being to merely provide visually distinctive so called color-coding; although technically speaking 'color' per'se can be devised into its scientific realms of 'hue' (shade}, 'intensity' {chroma), and 'value' (variable from white into gray into black).

Another object of this invention disclosure is to set forth an article according to preceding aspect, wherein it has also been found that the utility of this new dental-implant surgical-kit delivery-tray color-coding not only systematically eases the implant-dentist's task, but is also a method proving similarly advantageous to streamlining the work-task efficiency of the implant-dentist's support staff. For example, during routine-cleaning of the color coordinated arbor-tool implements prior to their reuse upon a subsequent implant-patient, the arbor-tools require stringent initial cleaning generally with plain soap and water, during which the individual arbor-tool implements become inadvertently mixed in scrambled disarray. Heretofore, upon reassembling the numerous seemingly look alike individual implements of a conventional dental-implant surgical-kit into its delivery-tray's holding receptacles, the dental-assistant would typically have to very closely examine the diminutive alpha-numeric ID-indicia inscribed upon the upper-shank of each arbor-tool {some persons having to resort to a magnifying-glass for reading clarity); as to thereby assure orderly arrangement for the implant-dentist's individual selection during the next operating session. Heretofore, this has been a time-consuming ordeal, dreaded even by an experienced staff-assistant; moreover, if the cleaning and reassembly of the surgical-kit arbor-tools were conducted by an inexperienced staff-assistant, their confused reassembly of the conventional non-colorized typically grayish titanium appearing arbor-tools can, much to the consternation of the implant-dentist, often become an utterly confusing disaster of disorganization.

However, the novel I-Dent™ System of color distinguished unidiameter-group segregation so clearly provides a systematic arrangement, that even the uninitiated dental-staffmember can deduce proper reassembly of the colorized arbor-tools upon the face of the uniquely color-coordinated surgical-kit delivery-tray, without the formerly tedious and laborious need for close visual inspection of each arbor-tool's shank ID-indicia, merely by following the simple logic of its organizational segregation into the generally three (two or more) different unidiameter color-matched groupings facilitated by the graphic color-groupings displayed upon the specially configured delivery-tray, This reassembly method is thus preferably conducted prior to moving the I-Dent™ delivery-tray into the autoclave-unit for final thermal-sterilization; whereupon the surgical-kit is resealed via a conventional detachable snap-on lid-closure member, and is thus ready for the implant-dentist's subsequent color-safeguarded patient osteotomy-site preparation usage.

Another object of this invention disclosure is to set forth an implant-dentist's surgical delivery-kit article according to preceding aspects, wherein is also provided a further option of color-coordinating both the factory-sealed vial-cap portion of the packaging-vial bearing the actual dental-implant; thereby enabling faster selection of the proper implant diameter from amongst the implant-dentist's drawer or cabinet stowed inventory (note that while a transparent vial is the preferred factory-packaging embodiment, other forms of factory-packaging should be regarded as within the purview of this reading). The dental-assistant now having to merely direct their attention to the preceding unidiameter-group coloration, thus also color-coded matched to the packaging-vial containing the same diameter of dental-implant for installation into the already screw-threaded endosseous pilot-hole of a patient's oral-cavity.

Another object of this invention disclosure according to the forgoing apparatus of the preceding aspects, is to set forth a further improvement defined as an optional albeit vital depth stop device, which is integrally formed proximally upon the medial (mid)-length region of all the implant-dentist's arbor-tool drill-bits. This radial-flange depth-stop device further streamlines procedures, as it eliminates need of an ungainly auxiliary depth-gauge (and another item needing to be kept track of), thus serving to passively safeguard the implant-dentist from inadvertently exceeding their pre-determined critical drilling-depth limitation requirement for the dental-implant prosthetic device the implant-dentist has ascertained to be appropriate for the patient. This vital albeit herein considered optional radial-flange depth-stop device, preferably also employs a convenient demarcation device in the form of an annular-detent provision, whereby the implant-dentist can eliminate the mental-distraction of referring to the obscure ID-indicia inscribed upon the arbor-tool shanks, and yet more readily confirming the particular length of a selected drill-bit by visually referencing the perimeter of the radial-flange. Since this efficient safeguarding strategy further liberates the implant-dentist from procedurally disruptive heretofore requirement of tediously examining the minute indicia each time they wish to move to a progressively longer drill-bit, the implant-dentist significantly improves their time-and-motion work-efficiency factor. For instance as a conjectural example only (noting that because particular colors and their order of arrangement can be adapted variously, specific colors are herein regarded as a factory/marketing engineering-design choice, thus actual specifying of particular colors remains outside the purview of this disclosure}, thus if the implant-dentist were to be using a green-tinted drill-bit they would thereby know via the novel I-Dent™ System coloration, that it is from amongst their small-sized unidiameter-group of arbor-tools. While if so equipped, further examination of the optional radial-flange perimeter surface will instantly inform them the particular length of the drill-bit; that is to say, a drill-bit's radial-flange bearing a single/annular-grove thus designates that it is the first (i.e.: shortest) drill-bit, and dual/annular-groves then designates that it is the second (i.e.: medium length) drill-bit, while a triad-annular-grove formation designates it is the third (i.e.: longest) drill-bit available from that unidiameter family of arbor-tools. Moreover, this same radial-flange drill-bit length identifier feature applies to all three of the preferred I-Dent™ System unidiameter-groups; although the radial-flanges themselves preferably vary in diameter proportionately to the variance in drill-bit diameters (i.e.: —a larger drill-bit having a larger radial-flange). Note also, that some applications of this annular demarcation technique may vary according to factory design-choice whereby for example the radial-flange of the shortest drill-bit may bear only a plain perimeter surface, thereby indicating it is of the shortest available, while the next longest drill-bit's radial-flange perimeter surface may bear a single/annular-groove indicates it is an intermediate length drill-bit, while a perimeter surface having a dual/annular-groove conveys to the implant-dentist that it is the longest drill-bit, hence, it is to be understood that specific annular-groove demarcation designations can vary according to factory engineering-design choice.

As an implant-dentist surgical-kit delivery-tray system, the disclosure hereof serves to clearly identify critical size differences among dental-implant oral-preparative components, eliminating reliance upon difficult to read minute ID-indicia, so as to thereby facilitate a simpler, faster and more accurate dental-osteotomy procedure. The system comprises an improved dental-implant delivery-tray reconfigured to present two or more unidiameter-groups which are visually segregated via discrete color discrimination. The system provides an arrangement of discretely color-coded arbor-tools which distinguish each unidiameter-group from the others, whereby the implant-dentist may simply progress in drilling depth steps only within a single unidiameter-group, or, they may progress via both drilling depth and diametrical steps, by translating to a larger unidiameter-group of a different color as the patient's osteotomy-site preparation advances toward desired final critical depth and diameter.

As an implant-dentist surgical-kit delivery-tray method, the disclosure hereof serves to set forth an easier, more accurate arbor-tool selection procedure, by essentially providing an improved delivery-tray configuration employing a cooperative set of two or more unidiameter-groups of arbor-tools which are each visually segregated via discrete color discrimination, by employing a small (diameter) unidiameter-group with a 1$^{st}$-color exclusively, and employing a medium {diameter) unidiameter-group with a different 2$^{nd}$-color exclusively and employing a large (diameter) unidiameter-group with a different 3$^{rd}$-color exclusively. Also, including graphic representation upon face of the delivery-tray via a band or field of matching color substantially surrounding each given discretely color-coded unidiameter-group, or alternately via a matching color circle (preferably in the form of a colored grommet) discretely surrounding individual arbor-tools of a given unidiameter-group. Thus, the safeguarded method supplies each unidiameter-group with a plurality of arbor-tools, including drill-bit length progressions of a common diameter, leading preferably forward toward the implant-dentist to a threading-tap of assured matching diameter (because the color is necessarily the same), whereby the implant-dentist may simply progress in drilling-depth steps only within a single unidiameter-group echelon, or they may orderly progress via bot drilling depth and diametrical steps by translating preferably laterally left-to-right to a larger diameter hence clearly differently colored-coded unidiameter-group as the patient's osteotomy-site preparation advances to desired final critical depth and diameter. The methodology also facilitates the option of the depth-limiting radial-flange device described above.

DETAILED DESCRIPTION OF THE INVENTION

Itemized Nomenclature References

Figures 1, 2:
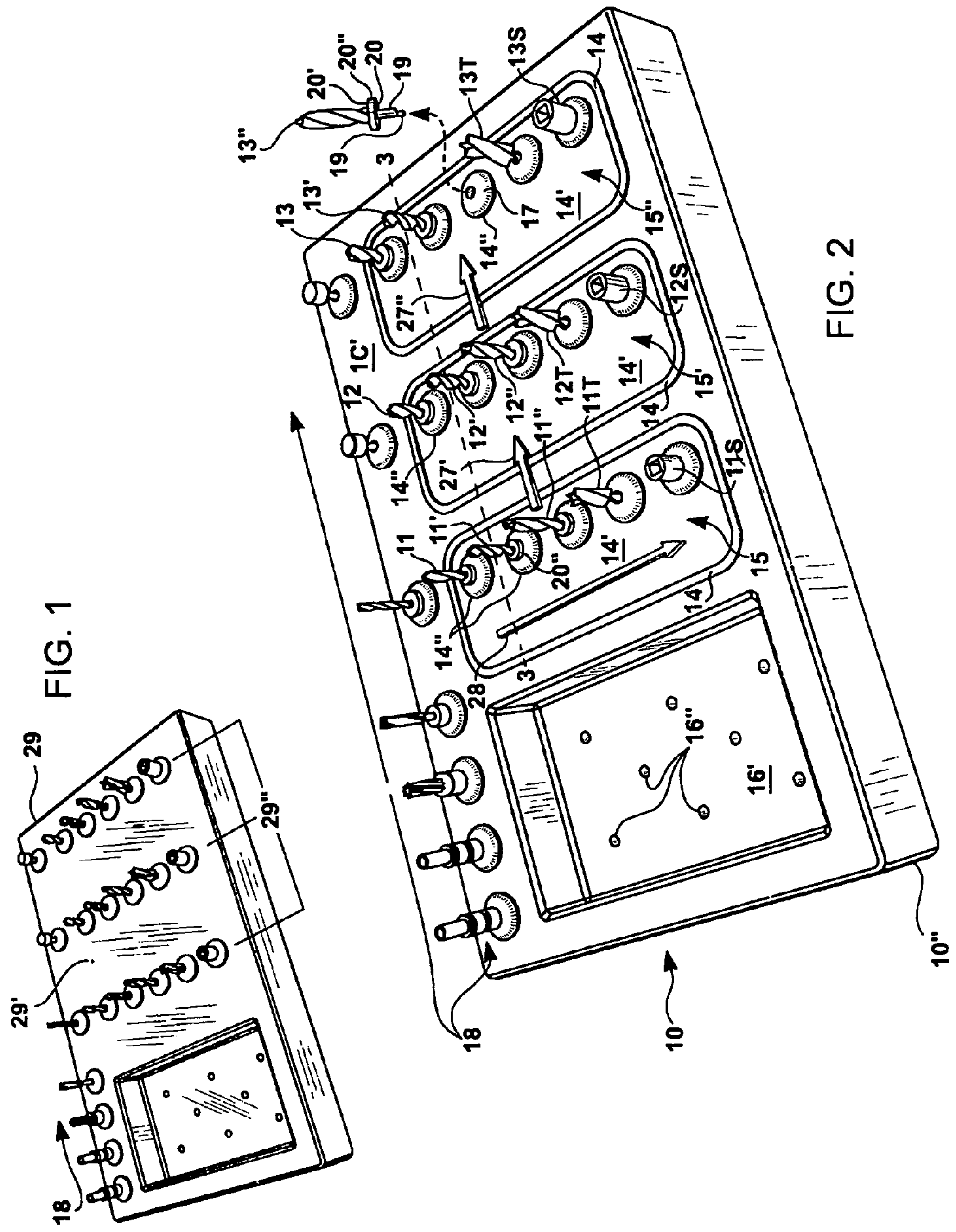
FIG. 1: is a perspective-view of the frontal upper-left portion of the implant-dentist's surgical-kit delivery-tray of conventional prior art design configuration, wherein all the rotary arbor-tools are confusingly of a common coloration.
FIG. 2: is an enlarged perspective-view of the frontal upper-left portion of the exemplified implant-dentist's surgical-kit and delivery kit of the present invention. Shown in the Figure is an array of arbor-tools that are color-segregated into a tertiary-grouping of discrete unidiameters, wherein the colors of the arbor-tools are arranged within an orderly matched surrounding field-color, whereby the diametrically larger drill-bits are shown preferably disposed toward the right of the delivery tray.

- 10, 10',10"—surgical-kit delivery-tray, face surface. perimeter-flange
- 11, 11', 11", 11T, 11S—1$^{st}$-color designation at small 3.4 mm unidiameter arbor-tools: dental drill-bit lengths: short/medium/long, threading-tap, socket
- 12, 12', 12", 12T, 12S—2$^{nd}$-color designation of medium 4.1 mm unidiameter arbor-tools: dental drill-bit lengths; short/medium/long, threading-tap, socket
- 13, 13', 13", 13T, 13S—3$^{rd}$-color designation of large 5.1 mm unidiameter arbor-tools: dental drill-bit lengths: short/medium/long, threading-tap, socket
- 14, 14', 14"—graphic color-key: hand/field/encirclement
- 15, 15', 15"—unidiameter-groups: 1$^{st}$-color=sml.-diam., 2$^{nd}$-color=med.-diam., 3$^{rd}$-color=large-diam.
- 16, 16', 16"—insert-panel, integral holding-dish standby-holes
- 17, 17', 17"—elastomeric grommet, retention-hole, tray/panel-hole
- 18—miscellaneous non-colorized arbor-tools
- 19, 19'—standard arbor-tool shank, standard dental-chuck coupling-tip
- 20, 20', 20", 20P—radial-flange: abutting-surface. undercut-surface, upper-side, perimeter
- 21, 21', 21'—single annular-groove double annular-grooving/triple annular-grooving
- 22, 22', 22"—color-coded vial-cap: 1$^{st}$-color=sml.-diam., 2$^{nd}$-color=med.-diam., 3$^{rd}$-color=large-diam.
- 23, 23', 23", 23L, 23R—standard vial, opening, sidewall, color-coded label, retainer-base
- 24, 24', 24"—conventional dental-implant: small-diam./medium-diam./large-diam.
- 25, 25', 25"—color-coded healing-cap: 1$^{st}$-color=sml.-diam., 2$^{nd}$-color=med.-diam., 3$^{rd}$-color=large-diam.
- 26, 26', 26"—soft-tissue, osseous. original natural teeth
- 27', 27"—unidiameter-group lateral translation stage ref-arrows-2$^{nd}$, 3$^{rd}$
- 28, 28', 28"—dental-bits: short/medium/long
- 29, 29', 29"—prior art: dental-tray, tray top-surface, common finished arbor-tools Initial references given by way of FIG. 1 'prior art' wherein is exhibited an implant-dentist's surgical-kit delivery-tray 29 which top-surface 29' is of conventional design organizational configuration and the array of arbor-tools 29" are of a common look-alike color regardless as to the subtle differences in drill-bit diameters. Hence, such ordinary configurations (exact arrangements and numbers of implements can vary considerably) are thus inefficient to use to the extent of posing the risk of serious confusion during selection of essentially look-alike arbor-tools set into a common panel area: thus unwittingly impeding the implant-dentist's need for seamless procedures and even imperiling patient safety during intense oral-operations.

In contrast, study of FIG. 2 reveals the greatly improved implant-dentist surgical-kit delivery-tray 10 having extensively reconfigured face surface 10' features, which employ color-coordinated guide-graphics to thoughtfully provide a major streamlining of time and motion procedures through judicious use of color-coding discretely coordinated with selected rotary implements to greatly simplify the formerly encumbered delivery-tray component selection task-procedures. More specifically, note how the arbor-tools are now logically segregated into three distinct corrals referred to herein as unidiameter-groups 15, 15', 15": the unidiameter-group 15 presenting the small-diameter arbor-tools all uniformly finished in a $1^{st}$-color, the unidiameter-group 15' presenting the medium-diameter arbor-tools all uniformly finished in a distinctively different: $2^{nd}$-color, and the unidiameter-group presenting the large-diameter arbor—tools all uniformly finished in a further distinctively different $3^{rd}$-color.

Figure 3:
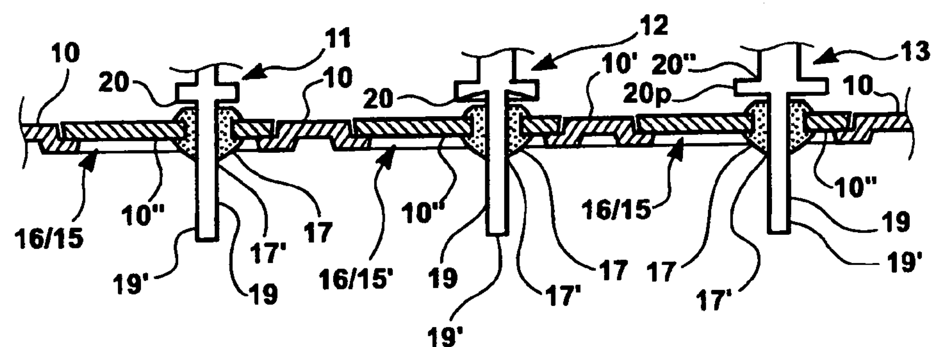
FIG. 3: is a semi-diagrammatic transverse cross-sectional elevation-view projected along the plane of reference 3:3 in FIG. 2, thereby alternatively in lieu of color-graphics exemplifying how three differently color-coded insert panels can be provided to surround the unidiameter arbor=tools of matching color.

Importantly, the three separate corral-like unidiameter-groups revealed in FIG. 2 are made visually distinct to the implant-dentist by means of graphic surround devices employing the same identical color as the arbor-tools which they present. These graphic devices can be as elementary as a simple narrow outline of color represented in FIG. 2 via band 14, or a broadly surrounding field 14', or merely a discrete color encirclement 14" (which may be an actual holding grommet 17 molded of a color matching the unidiameter arbor-tool which it is presenting). Of these exemplified graphic devices, the field surround option 14' may offer the most interesting design potential as FIG. 3 shows how it can actually be implemented in the form of a transparent plastic injection-molded insert-panel 16, shown therein in three distinctively different colorations, such as a green-tint matching the arbor-tools color of the small unidiameter-group 15, an amber-tint matching the arbor-tools color of the medium unidiameter-group 15', and a violet-tint matching the arbor-tools color of the large unidiameter-group 15"; and if one of the unidiameter-groups presents arbor-tools which are left in their natural metal-finish state, the insert-panel 16 can likewise be regarded as tantamount to ‘color-coded’ us an untinted transparent polycarbonate-plastic (highly autoclave-temperature resistant).

Within each of the exemplified unidiameter-groups of FIG. 2 are included traditional incremental progressions (action ref.-arrow 27) of drill-bit lengths, for example, in the rearmost position of the unidiameter-group 15 representing only a $1^{st}$ color of 3.4 mm diameter arbor-tools is shown the shortest drill-bit 11 which is preferably 10 mm long, then the next drill-bit 11' is preferably 12 mm long, followed by the longest drill-bit 11" preferably 14 mm long, and next in view is the associated dental-osseous thread-tap 11T, and finally the nearest rotary-tool being the cooperative 3.4 mm wrench socket 11S. It is important to understand that the very same logical progressions are provided in the next (laterally toward the right) two adjoining albeit different $2^{nd}$-color 4.1 mm unidiameter-group 15', and different $3^{rd}$-color 5.1 mm unidiameter-group 15"; therefore, the implant-dentist can also translate laterally (action ref.-arrows 27' and 27") as desired, confident in knowing that their drilling depth will remain constant unless they intentionally elect to progress further via ref.-arrow 27. Moreover, if desired, the three exemplified different hue-colors can also be made to vary in chroma, according to their respective progressions in depth; thus the actual hue-colors remain the same, although they ail appear to vary in surrounding field shade from a lighter-shade at rear positions 11/12/13 toward a darker-shade of the same hue-color for field surround positions 11"/12"/13".

This constant-hue/variable-shade effect is basically analogous to the way a printer’s Color-wheel chart designed, with white (max.-intensity) at center-axis of the Color-wheel and the different colors surrounding the axis somewhat like spokes of a wheel, with the rim being essentially black (min.-intensity). The notion being to provide not only the different hue colors from left-to-right, but optionally different gradations of those discrete colors from rear-to-front as well. However, the primary intent this disclosure set forth the basic notion of different distinguishing colors (hues) according to the different exemplified unidiameter-groups 15/15'/15": the additional optional provision of variable hue-values within each of the unidiameter-groups being merely a further refinement.

Note also that while FIG. 2 shows the arbor-tools furnished with the novel depth-stop radial-flange having a perimeter 20" diameter approximately twice the diameter of its host drill-bit diameter, it is to be understood that the improved delivery-tray 10 will also serve dental arbor-tools not equipped with the radial-flange; hence appearing substantially like the conventional arbor-tools shown in FIG. 1, with the major exception that the arbor-tools of FIG. 2 necessarily feature the essential color-coding finish (with or without the radial-flange option). At far right of FIG. 2 is shown a removed exemplified drill-bit 13", which is tipped at an angle whereby the radial-flange abutting-surface 2, proximal shank 19, and exemplified coupling tip 19' portion are in view: and it is understood that the design the twist-drill flutes and coupling-tips can vary substantially according to manufacturing design choice, and therefore bare no significance to the disclosure.

Figure 4:
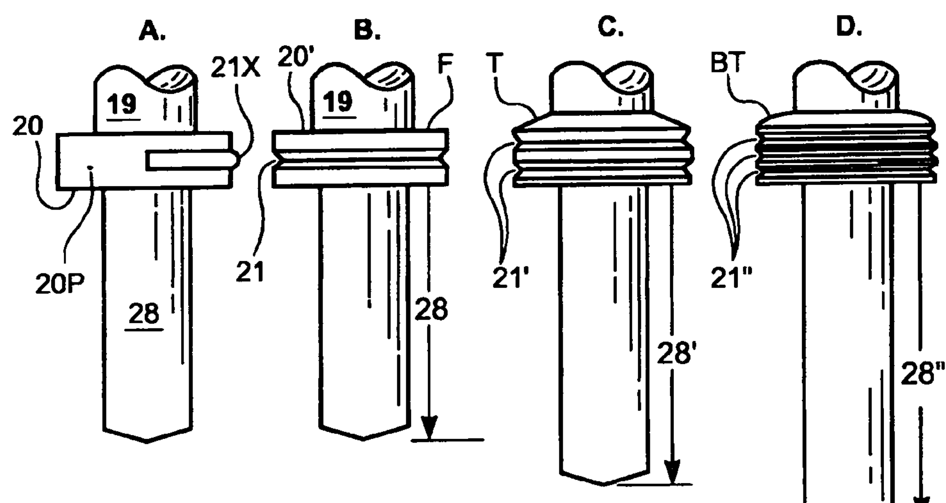
FIG. 4: is a quadric-lateral series of side/elevation-views showing how different annular demarcations provided upon the perimeter of the radial-flange depth-stop apparatus, in combination, with color-coding, facilitating faster positive identification while selecting from among the different incremental lengths of drill-bits.

There remain subtle, however vital other differences which are to become herein more evident and understood as important improvements. For example, in FIG. 4 is shown a triad of substantially conventional dental-implant factory-packaging in the form of generally transparent glass or plastic vials 23 having novel color-coded injection-molded plastic vial-caps 22, 22; and 22", each vial-cap being intimately adapted to and preferably press-fitting (a mild friction-fit sufficient to maintain a hermetic-seal) into the vial opening 23, each vial preferably including its own discretionary matching color-coded labels 23L, 23L' and 23L “applied to the respective sidewall 23” of the individual conventional vials (corresponding to the matching color-coded vial-caps). Shown partially withdrawn in FIG. 4, thus protruding-up from each of the vials 23, are the sterilely contained different unidiameter-group dental-implants 24, 24' and 24" which can compromise both the $1^{st}$-stage (S') and $2^{nd}$-stage (S") portions of the dental-implant, and are optionally factory-assembled via a coaxial Allen/assembly-screw (the upper-tip of which is shown atop the abutment-post portion of the indicated $2^{nd}$-stage (S")). Also shown conventionally pressed into the normally enclosed end of each vial-cap 20, 20', and 20" are unique discretely color-coded but otherwise conventional so-called healing-caps 25, 25' and 25", each essentially comprising a machine-screw which male screw-threaded shank portion is commonly pressed into a retainer-bases 23R, and thus become protectively enclosed within the vial. Other than the novel color-coding feature, this exemplifies a conventional packaging arrangement facilitating convenient accessibility of the healing-cap from each vial-cap’s retainer-base 23R once the implant-dentist has installed the $1^{st}$-stage dental-implant portion, and therefore must seal-off the longitudinal central-core of the $1^{st}$-stage primary/dental-implant to prevent problematical foreign matter entering therein during osseointegration of the $1^{st}$-stage. Each healing-cap thus employs a distinct color matching the color of its respect vial-cap; and whereby later, when the implant-dentist decides the osseointegration of the earlier installed dental-implant is satisfactorily merged with the patient's osseous, the implant-dentist (or a subsequent dentist dealing primarily with preparation of crowns) has merely to observe the particular color (hue) of the exposed healing-cap 25, 25', and 25" as to thereby which $2^{nd}$-stage implant portion to select for attachment upon the ensconced $1^{st}$-stage dentist-implant member. The $2^{nd}$-stage implant portion rises above the patient's soft gum-tissue, and generally features an abutment-post portion serving to solidly support the final realistic appearing ceramic prosthetic-tooth crown.

Study of FIG. 4 clearly shows the radial-flange depth-stop provision which is advantageously positive-acting in drilling limitation, as compared to passively-acting conventional dental drill-bits featuring mere incremental depth reference demarcations of one sort or another upon their medial-shank region. This depth-limiting radial-flange is vital in keeping with the basic procedural safeguarding premise of the most preferred embodiment. As initially revealed in FIG. 2, the radial-flange configuration preferably presents horizontally flat disk area portion, referred to as abutting-surface 20: and because this surface serves to interface direct upon the patient's bony oral-osseous (see FIG. 6). It is considered important this abutting-surface 20 not be tapered up from the drill-flute region, as that would tend to provide a less positive depth-limit action, although an alternate reverse under-cut 20' formation (e.g.: which cross-section is revealed at center of FIG. 3) is an acceptable alternative embodiment.

The FIG. 4 presentation reveals an alternate optional embodiment for the radial-flange's perimeter surface 20P which until now has been shown as merely plain, remiss of special markings; thus here are shown several iterations of the optional radial-flange embodiment with a practicable annular demarcation means, serving to readily confirm at a glance by the implant-dentist, the particular length of a selected dental drill-bit: thereby obviating need for interruptive reference to the difficult to read alpha-numeric indicia inscribed upon the arbor-tool's upper-shank surface. Beginning at far left, exhibit-A, shows a side-view of a dental drill-bit having the depth-limiting radial-flange which left-perimeter 20P is by way of comparison, of plain unadorned design, while for convenience of illustration the right-perimeter portion is shown with an exemplified integrally formed annular-rib 21X device, which is for purposes of this disclosure regarded at tantamount in function to the exhibit-B iteration, which, perimeter surface is provided with a single annular-groove 21. Note that all FIG. 4 embodiments can thus employ either the integral annular-rib 21X or annular-groove 21 configuration, albeit preferably, consistent as to implementation of either embodiment according to factory engineering-design choice. Thus progressing still further toward the right, exhibit-C, shows the perimeter surface provided with a double annular-groove 21', while the final exhibit-D, at far right, feature s a triple annular-groove 21". Therefore, these preferred radial-flange demarcations (whether formed inwardly or optionally outwardly), in combination with the color-coding system, represent a swift yet sure means by which the implant-dentist can work among their various arbor-tools with absolute confidence, while virtually liberated from the heretofore problematical (time and motion wasting distraction) procedure of having to stop to closely examine a drill-bit's obscure indicia in order to confirm that the drill-bit they've selected is indeed both the correct diameter and length.

Note also in FIG. 4 that since the opposing upper-surface 20" of the radial-flange serves no particular function, it may be of any desired circular formation such as flat F, tapered T or ball-tapered B1. Moreover, FIG. 4 supports the notion that the differently color-coded radial-flange equipped dental drill-bits may be worked in lateral coordination without confusion, when taken relative to the FIG. 2 delivery-tray face surface 10' graphics (e.g.: encircling discretely color-coded bands 14 identifying the three exemplified diameter-groups 15, 15' and 15") during the ostectomy procedure. Thereby advantageously eliminating heretofore need of generally fidgeting with an ungainly depth gauge, in which a separate probing-tool necessitates repeated removal of the trauma imposing dental drill-bit, and undesirable if tedious procedure. Since conventional dental drill-bits bearing mere depth reference-markings, offer no actual positive means of preventing the implant-dentist exceeding of a critical drilling-depth restrictions, generally determined in conjunction with intermittent X-ray visualizations for example: then it can thus be understood the utility value of discretely color-coded unidiameter-grouped dental arbor-tool drill-bits, each equipped in novel combination with this depth-limiting radial-flange; providing a uniquely safeguarded oral-osteotomy procedures.

Figure 5:
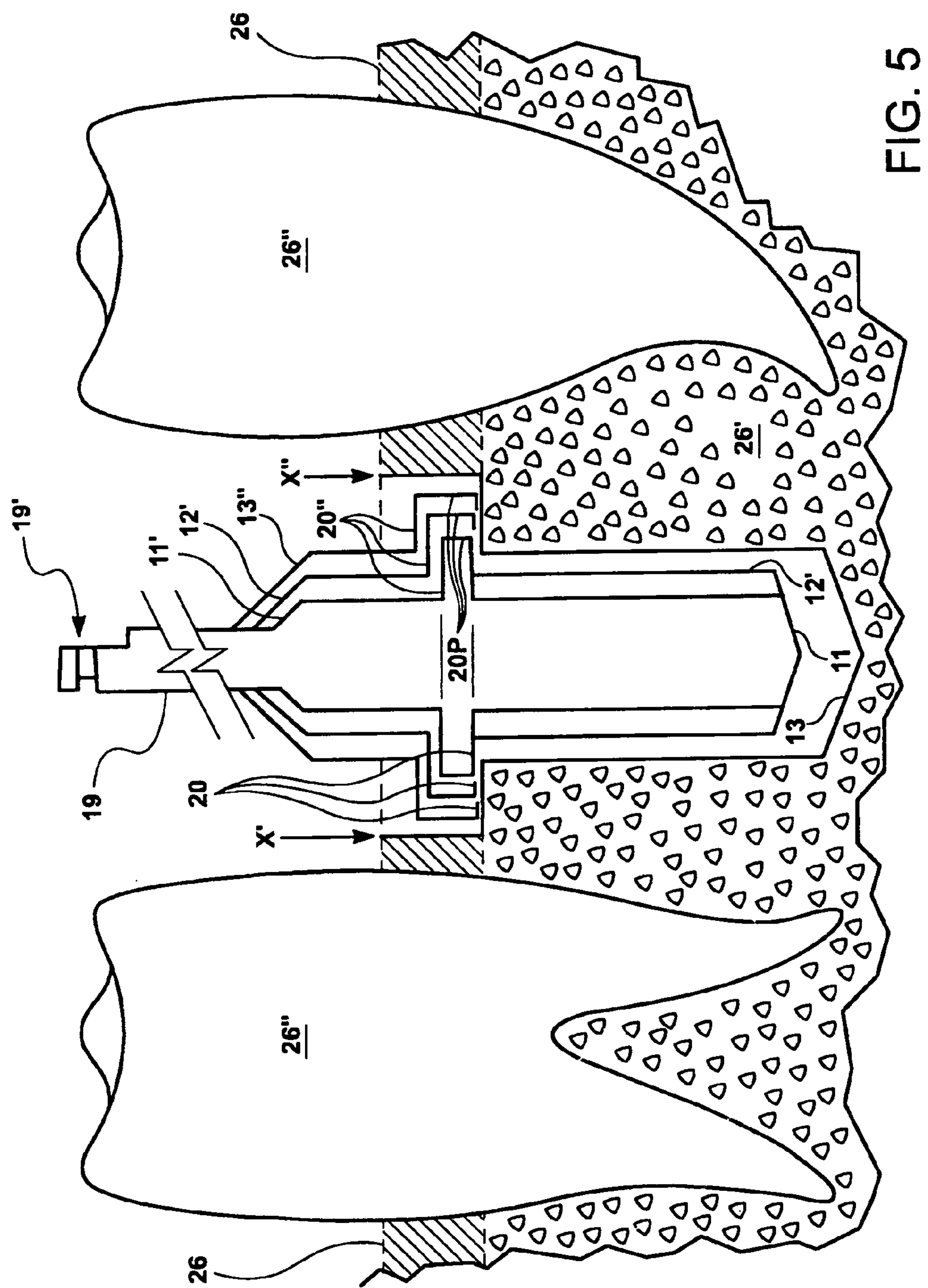
FIG. 5: is a diagrammatic cross-sectional side/elevation-view representation of a dental-implant osteotomy-site procedure, wherein is demonstrated a triple superimposed dental drill-bit procedure of diametrically incremental-steps, showing how the integrally-formed radial-flange option maintains a constant drilling-depth among all three diametrical progressions.

Next, study of FIG. 5 shows an exemplified dental drill-bit 11' having first bored down into the patient's osseous 26', once the comparatively soft-tissue 26 (gum material) is surgically relieved at circumscribed region residing between indicators—X' and X". Whereupon the implant-dentist may determine they need to laterally transfer 27' (see FIG. 2) to the next larger diameter albeit the same depth, selects drill-bit 12' from adjacent differently color-coded unidiameter-group 15' and completes that drilling procedure, but then after further evaluation determines they should make a further lateral transition 27" into unidiameter-group 15" via selection of further differently color-coded dental drill-bit 13" via final progression 27. At this advanced juncture, the implant-dentist completes the oral-ostechomy procedure by chasing down the final pilot-hole bore via threading-tap 13T (see FIG. 2), thereby having completed preparation of the osteotomy-site for initial installation of the actual conventional stage-one dental-implant prosthesis for subsequent osseointegration.

Thus, it is readily understood how the preferred and generic-variant embodiments of this invention contemplate performing functions in a novel way not heretofore available nor realize. It is implicit that the utility of the foregoing adaptations of this invention are not necessarily dependent upon any prevailing invention patent: and, while the present invention has been well described hereinbefore by way of certain illustrated embodiments, it is to be expected that various changes, alterations, rearrangements, and obvious modifications may be resorted to by those skilled in the art to which it relates, without substantially departing from the implied spirit and scope of the instant invention. Therefore, the invention has been disclosed herein by way of example, and not as imposed limitation, while the appended Claims set out the scope of the invention sought, and are to be construed as broadly as the terminology therein employed permits, reckoning that the invention verily comprehends every use of which it is susceptible.

Accordingly, the embodiments of the invention in which an exclusive property or proprietary privilege is claimed, are defined as follows.

What is claimed of proprietary inventive origin is:

1. A dental-implant surgical delivery-kit that reduces or eliminates potential diametrical sizing errors during use comprising:

a tray having a face surface with at least five areas for storage of dental implant tools;

a first corral, a second corral and a third corral each housing arbor-tools said corrals having discrete receiver-ports for receiving said arbor-tools, wherein said arbor-tools in a corral are a unidiameter-group having at least three drill-bits oriented in order of progressively increasing length, a thread-tap and a socket wrench, wherein each of said arbor-tools in a corral have the same color indicator, wherein each corral has a color matching said color of said arbor-tools in said unidiameter-group, wherein said corrals are oriented in order of progressively increasing diameter, wherein each of said drill-bits has a depth-limiting radial flange, wherein said radial-flange has one or more annular-grooves, wherein said at least three drill-bits have a sequentially increased number of annular-grooves with increasing depth;

an insert panel that is autoclave-temperature resistant for receiving said arbor-tools following use; and a miscellaneous storage area for housing additional said dental implant tools.

2. The dental-implant surgical delivery-kit according to claim 1, wherein said first corral and said arbor-tools in said first corral have a $1^{st}$ color exclusively, said second corral and said arbor-tools in said second corral have a $2^{nd}$ color exclusively, and said third corral and arbor-tools of said third corral have a $3^{rd}$ color exclusively.

3. The dental-implant surgical delivery-kit according to claim 2, further comprising a $1^{st}$ stage dental-implant body housed in a package wherein said package comprises a cap and a vial wherein said vial has a label, wherein said cap and/or said vial label have a $1^{st}$ color exclusively, wherein said $1^{st}$ stage dental-implant body is also color-coded coordinated to thereby be readily identified as to a specific unidiameter-group simply by reference to the vial vial's correspondingly matching color-coded vial-cap or vial-label.

4. The dental-implant surgical delivery-kit according to claim 3, wherein said $1^{st}$ stage dental-implant body further comprises a healing cap, wherein said healing cap is color-coded to match its associated unidiameter-group such that when said $1^{st}$ stage dental-implant is implanted said healing cap is exposed and uniquely identified for future reference by its color and enabling them implant-dentist to later at a glance thereby confidently identify an appropriately sized $2^{nd}$ stage dental-implant once sufficiently osseointegrated.

* * * * *